United States Patent
Abillard et al.

(10) Patent No.: US 8,759,594 B2
(45) Date of Patent: Jun. 24, 2014

(54) METHOD FOR PRODUCING 1,6-HEXANEDIOL BY HYDROGENATION OF OLIGO- AND POLYESTERS

(75) Inventors: Olivier Abillard, Mannheim (DE); Rolf Pinkos, Bad Duerkheim (DE); Gerd-Dieter Tebben, Mannheim (DE); Tilman Sirch, Schifferstadt (DE); Daniel Urbanczyk, Darmstadt (DE); Heiko Urtel, Bobenheim-Roxheim (DE); Rolf Tompers, Mannheim (DE)

(73) Assignee: BASF SE, Ludwigshafen (DE)

( * ) Notice: Subject to any disclaimer, the term of this patent is extended or adjusted under 35 U.S.C. 154(b) by 221 days.

(21) Appl. No.: 13/258,207

(22) PCT Filed: Mar. 29, 2010

(86) PCT No.: PCT/EP2010/054114
§ 371 (c)(1),
(2), (4) Date: Sep. 21, 2011

(87) PCT Pub. No.: WO2010/115759
PCT Pub. Date: Oct. 14, 2010

(65) Prior Publication Data
US 2012/0035399 A1 Feb. 9, 2012

(30) Foreign Application Priority Data
Apr. 8, 2009 (DE) .......................... 10 2009 002 280

(51) Int. Cl.
*C07C 27/00* (2006.01)

(52) U.S. Cl.
USPC .......................................... 568/865; 568/861

(58) Field of Classification Search
None
See application file for complete search history.

(56) References Cited

U.S. PATENT DOCUMENTS

| | | | |
|---|---|---|---|
| 3,524,892 A | 8/1970 | Horlenko et al. | |
| 3,933,930 A * | 1/1976 | Dougherty et al. | 568/864 |
| 5,696,303 A * | 12/1997 | Darsow et al. | 568/864 |
| 6,037,504 A * | 3/2000 | Darsow et al. | 568/864 |
| 6,288,286 B1 | 9/2001 | Stein et al. | |
| 7,510,591 B2 * | 3/2009 | Huber-Dirr et al. | 75/233 |
| 2006/0178539 A1 | 8/2006 | Huber-Dirr et al. | |
| 2008/0064882 A1 | 3/2008 | Huber-Dirr et al. | |
| 2008/0207953 A1 | 8/2008 | Houssin et al. | |
| 2010/0056364 A1 | 3/2010 | Huber-Dirr et al. | |

FOREIGN PATENT DOCUMENTS

| | | |
|---|---|---|
| CA | 2 311 589 A1 | 6/1999 |
| CN | 1281425 A | 1/2001 |
| DE | 1 255 650 | 12/1967 |
| DE | 1 951 250 | 4/1970 |
| DE | 197 38 464 | 3/1999 |
| EP | 0 661 255 | 7/1995 |
| EP | 0 673 909 | 9/1995 |
| EP | 0 721 928 | 7/1996 |
| EP | 0 847 979 | 6/1998 |
| EP | 0 922 688 | 6/1999 |
| JP | 03-115237 | 5/1991 |
| JP | 07-165643 | 6/1995 |
| JP | 2002-516889 | 6/2002 |
| JP | 2005 8586 | 1/2005 |
| JP | 2009-502746 | 1/2009 |
| WO | 99 03801 | 1/1999 |
| WO | WO 99/31035 A1 | 6/1999 |
| WO | 2004 085356 | 10/2004 |
| WO | 2006 005505 | 1/2006 |
| WO | 2007 006719 | 1/2007 |

OTHER PUBLICATIONS

Weissermel, K., et al., "Industrielle Organische Chemie," pp. 261-267, (1998) (German) and corresponding passage pp. 237-245 of the English translated edition.
International Search Report Issued Nov. 19, 2010 in PCT/EP10/054114 Filed Mar. 29, 2010.
U.S. Appl. No. 13/133,006, filed Jun. 6, 2011, Abillard, et al.
U.S. Appl. No. 13/258,166, filed Sep. 21, 2011, Pinkos, et al.
U.S. Appl. No. 13/257,496, filed Sep. 19, 2011, Pinkos, et al.
U.S. Appl. No. 13/226,049, filed Sep. 6, 2011, Abillard, et al.
U.S. Appl. No. 13/381,116, filed Dec. 28, 2011, Kunst, et al.
Office Action issued Jul. 25, 2013 in Chinese Patent Application No. 2010800147985 (submitting English translation only).
Office Action issued Apr. 1, 2014, in Japanese Patent Application No. 2012-503963 filed Mar. 29, 2010 (with English translation).

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The present invention relates to a process for hydrogenating oligo- and/or polyesters obtainable by esterifying a DCS with a diol or diol mixture, said hydrogenation being performed in the presence of a catalyst whose catalyst precursor comprises copper oxide, aluminum oxide and at least one oxide of lanthanum, of iron, of tungsten, of molybdenum, of titanium or of zirconium, and to a process for preparing 1,6-hexanediol by catalytically hydrogenating ester mixtures which comprise, as main components, oligo- and polyesters of adipic acid and 6-hydroxycaproic acid, and are obtained by esterifying DCS with diols, especially 1,6-hexanediol or diol mixtures.

16 Claims, No Drawings

METHOD FOR PRODUCING 1,6-HEXANEDIOL BY HYDROGENATION OF OLIGO- AND POLYESTERS

The present invention relates to a process for hydrogenating oligo- and/or polyesters obtainable by esterifying a dicarboxylic acid solution (DCS) with a diol or diol mixture, said hydrogenation being performed in the presence of a catalyst whose catalyst precursor comprises copper oxide, aluminum oxide and at least one oxide of lanthanum, of iron, of tungsten, of molybdenum, of titanium or of zirconium, and to a process for preparing 1,6-hexanediol by catalytically hydrogenating ester mixtures which comprise, as main components, oligo- and polyesters of adipic acid and 6-hydroxycaproic acid, and are obtained by esterifying DCS with diols, especially 1,6-hexanediol or diol mixtures.

There is a great need for 1,6-hexanediol, which is a sought-after monomer unit used predominantly in the polyester and polyurethane sectors.

H.-J. Arpe describes, in Industrielle organische Chemie [Industrial Organic Chemistry], 6th edition 2007, WILEY-VCH-Verlag, page 267, penultimate paragraph, the esterification of adipic acid and the catalytic hydrogenation of the diesters to 1,6-hexanediol.

WO 2004/085356 discloses the hydrogenation of dimethyl adipate, which was prepared from adipic acid and methanol as a monoalcohol, to give 1,6-hexanediol. The fixed bed catalyst used comprised copper, aluminum oxide and lanthanum oxide. Hydrogenation was effected at 240° C./200 bar. According to example 2, ester conversions of 98 to 99% were achieved. The hydrogenation output comprised 1,6-hexanediol contents of 57% by weight and 62% by weight. 62% by weight corresponds approximately to a 1,6-hexanediol yield of 96%. A disadvantage is the use of pure adipic acid, owing to its cost, and the costly and inconvenient removal of large amounts of methanol from the hydrogenation output. Moreover, methanol losses occur as a result of dimethyl ether formation. The hydrogenation of oligo- and/or polyesters of adipic acid and 6-hydroxycaproic acid is not described.

Instead of pure adipic acid, dicarboxylic acid solution (DCS) has also been used as a starting material for the preparation of 1,6-hexanediol. It is obtained as a waste product in the oxidation of cyclohexane with air to give cyclohexanone and cyclohexanol, by extraction of the oxidized mixture with water.

The integrated system with production plants for preparing cyclohexanol and cyclohexanone and the utilization of the DCS waste product as a starting material for the preparation of 1,6-hexanediol leads to favorable feedstock costs compared to pure adipic acid. It also constitutes environmentally friendly utilization of a waste product.

The working example of DE 196 07 954 describes esterifying dewatered dicarboxylic acid with methanol and hydrogenating the ester mixture, after removal of low boilers, in the presence of catalysts comprising copper, zinc oxide and aluminum oxide to 1,6-hexanediol and methanol. At 220° C. and 220 bar, the ester conversion was 99.5%, the 1,6-hexanediol selectivity>99%.

A disadvantage is the use of methanol, which has to be removed and recycled, and the side crushing strength of the hydrogenation catalyst, which decreases in the course of the hydrogenation.

The use of diols, especially of alpha,omega-diols, as esterification alcohols constitutes an advantage over monoalcohols. The losses of esterification alcohol are reduced, and the workup of the hydrogenation output is simplified.

EP-A 922 688 describes the hydrogenation of oligoesters which have been prepared from adipic acid and 1,6-hexanediol. Hydrogenation was effected in the presence of zinc oxide-free copper catalysts which comprised manganese oxide and aluminum oxide and at least one oxide of metals of transition group VI. The hydrogenation according to example 2 was performed at 230° C. and 300 bar. The 1,6-hexanediol content of the hydrogenation output was 97.1%. The use of DCS as a starting material for the preparation of the oligoesters is not described in EP-A 922 688.

The existing prior art shows that adipic diesters prepared from pure adipic acid and monoalcohols, DCS and monoalcohols, and oligo- and polyesters prepared from pure adipic acid and pure 1,6-hexanediol can be hydrogenated to 1,6-hexanediol with high yields of about 96 to 99%. For the hydrogenation, catalysts based on copper and zinc oxide, copper and aluminum oxide or copper, aluminum oxide and zinc oxide were used.

It is also already known to hydrogenate oligo- and/or polyesters prepared proceeding from DCS and 1,6-hexanediol or diol mixtures catalytically to 1,6-hexanediol. This variant possesses the advantage in principle that the 1,6-hexanediol target product or diol mixtures comprising predominantly 1,6-hexanediol from the process can be used for the esterification of the dicarboxylic acid. The catalysts used for the hydrogenation of the oligo- and polyesters and/or the 1,6-hexanediol yields achieved are, however, still unsatisfactory.

For instance, U.S. Pat. No. 3,524,892 discloses oxidizing cyclohexane with air to give a mixture of cyclohexanone, cyclohexanol, unconverted cyclohexane, adipic acid and 6-hydroxycaproic acid, and extracting the reaction product of the oxidation with water. Phase separation affords an organic phase and an aqueous phase. The organic phase consists predominantly of cyclohexane, cyclohexanol and cyclohexanone, and is at least partly recycled into the oxidation stage. The aqueous phase comprises predominantly adipic acid and 6-hydroxycaproic acid. It is dewatered and reacted with pure 1,6-hexanediol to give oligoesters. The oligoesters are hydrogenated at 260 to 275° C. and 275 to 330 bar in the presence of copper chromite catalysts to give 1,6-hexanediol as the main product.

A disadvantage is the use of catalysts which, like copper chromite, are toxic owing to their chromium content and necessitate a high level of complexity in the operation of the hydrogenation and in the disposal of spent catalysts and chromium-containing by-products. Moreover, the high hydrogenation temperature and the high hydrogenation pressure document a lack of catalyst activity which leads to enhanced by-product formation. The yield of 1,6-hexanediol by this process is not described.

EP-A 661255 describes the hydrogenation of ester mixtures which have been prepared by esterifying DCS with 1,6-hexanediol or with diol mixtures obtained in the hydrogenation. The hydrogenation was effected batchwise at 250 to 300° C. and 150 to 300 bar. The catalysts used were suspension catalysts comprising copper and zinc oxide. In the working examples, hydrogenation was effected at 280° C. and 280 bar. Figures for 1,6-hexanediol yields, ester conversions or catalyst consumption numbers are not described.

Disadvantages are the high hydrogenation temperature, the high hydrogenation pressure and the difficult removal of the suspended hydrogenation catalyst from the hydrogenation output.

JP 2005/008586 differs from EP-A 661 255 in particular in that fixed bed catalysts are used. The fixed bed catalysts used are $CuO/ZnO$, $CuO/ZnO/Al_2O_3$, $CuO/SiO_2$, $CuO/ZrO_2$ and $CuO/Cr_2O_3$ catalysts, as described on page 11, paragraph

[0018]. These are catalysts as have also already been used with high yields for the hydrogenation of adipic esters prepared from pure adipic acid and monoalcohols, esters of DCS with monoalcohols, and oligo- and polyesters prepared from pure adipic acid and pure 1,6-hexanediol. Hydrogenation was effected at 190 to 250° C. and 1 to 10 MPa. An increase in the pressure does not lead to any improvement in the reaction result, as described at page 13, in paragraph [0022], lines 3 to 4.

At page 15, paragraph [0026], the preparation of the oligo-/polyester mixture is described as follows: product freed of cyclohexanol and cyclohexanone from the liquid phase oxidation of cyclohexane was purified with aqueous sodium hydroxide solution. The aqueous solution of sodium carboxylates removed was acidified with sulfuric acid. The carboxylic acids released were extracted with methyl i-butyl ketone. The carboxylic acid mixture obtained after removal of the extractant, which no longer corresponds to the DCS obtained after oxidation and extraction with water, since products including cyclohexanol, 1,2- and 1,4-cyclohexanediol, cyclohexanone, cyclohexanedione and low-value alcohols have been removed, was esterified with a mixture of 1,6-hexanediol, 1,5-pentanediol and monohydric alcohols such as pentanol and butanol.

A disadvantage of JP 2005/008586 is that, according to working examples 1 to 5 (in examples 1 to 3 and 5 CuO/ZnO, in example 4 CuO/SiO$_2$, as the catalyst), only 1,6-hexanediol yields between 84 and 89% were achieved at conversions of only 84 to 91%. A further disadvantage is that the 1,6-hexanediol yields specified are achieved only when the hydrogenation was performed in the presence of a low-value monoalcohol such as methanol. When no low-value monoalcohol is used, the 1,6-hexanediol yield is low, as described at page 12, paragraph [0019], the last three lines.

The esterification of a DCS with diols or diol mixtures gives rise to oligomeric esters of different composition. The hydrogenation thereof makes high demands on the appropriate catalyst, since it must not become poisoned and must nevertheless exhibit a high activity and selectivity. Proceeding from the prior art, it is therefore not obvious that catalysts which in the hydrogenation of monomeric esters prepared by the reaction of pure adipic acid with low-value alcohol, for example methanol, also conduct the hydrogenation of esters which have been prepared from a complex DCS by esterification with a diol or diol mixture to similarly good yields and purities of the end product.

It was therefore an object of the present invention to provide a process for hydrogenating oligo- and polyesters obtainable by esterifying a DCS with a diol mixture in the presence of a catalyst. The catalyst used for the hydrogenation should possess a high hydrogenation activity in order to achieve a virtually complete oligo- and/or polyester conversion with high 1,6-hexanediol yield and selectivity. The catalyst should additionally permit a high service life with constant conversion and little reduction in side crushing strength. Moreover, it should not form any secondary components which significantly complicate the purification of the 1,6-hexanediol. Finally, it should not comprise any toxic components which complicate working with this catalyst and the disposal thereof.

This object is achieved by a process for hydrogenating oligo- and/or polyesters obtainable by esterifying a dicarboxylic acid solution with a diol or diol mixture, said hydrogenation being performed by means of a shaped catalyst body whose precursor is preparable by a process in which (i) an oxidic material comprising copper oxide, aluminum oxide and at least one of the oxides of lanthanum, of tungsten, of molybdenum, of titanium, of zirconium or of iron is provided,
(ii) pulverulent metallic copper, copper flakes, pulverulent cement, graphite or a mixture thereof is added to the oxidic material,
(iii) the mixture resulting from (ii) is shaped to a shaped body, said oxidic material being obtainable by simultaneous or successive precipitation of the active copper component, of the aluminum component and of the component of at least one of the oxides of lanthanum, of tungsten, of molybdenum, of titanium or of zirconium, and subsequent drying and calcination, and the shaped catalyst body is calcined once again after the shaping in step (iii).

The present invention relates to a process for hydrogenating oligo- and polyesters of the DCS to diols using specific shaped catalyst precursor bodies for the hydrogenation, the shaped catalyst precursor bodies comprising, as well as copper oxides and aluminum oxides, at least one oxide of lanthanum, of tungsten, of molybdenum, of titanium, of zirconium or of iron, and metallic copper, copper flakes, pulverulent cement, graphite or a mixture. The DCS is esterified by means of diols which are selected from the group of glycerol, trimethylolpropane, propylene glycol, ethylene glycol, 1,3-propanediol, 1,4-butanediol, 1,5-pentanediol, 1,6-hexanediol, 1,2-cyclohexanediol, 1,4-cyclohexanediol, 1,8-octanediol, 1,10-decanediol, 1,12-dodecanediol or mixtures of these diols. Preference is given to 1,4-butanediol, 1,5-pentanediol, 1,6-hexanediol, 1,2-cyclohexanediol, 1,4-cyclohexanediol or mixtures of these diols. Preference is given to the esterification of the DCS with the aid of 1,6-hexanediol to give oligo- and/or polyesters.

Among the oxides of lanthanum, of tungsten, of molybdenum, of titanium or of zirconium, lanthanum oxide is preferred.

Iron oxide means iron(III) oxide.

In preferred embodiments, the inventive shaped bodies are used in the form of unsupported catalysts, impregnated catalysts, coated catalysts and precipitation catalysts.

The catalyst used in the process according to the invention for the hydrogenation is notable in that the active copper component, the aluminum component and the component of at least one of the oxides of lanthanum, of tungsten, of molybdenum, of titanium or of zirconium are precipitated simultaneously or successively, preferably with a soda solution, then dried, calcined, tableted and calcined once again.

The following precipitation method is especially useful:
A) a copper salt solution, an aluminum salt solution and a solution of at least one salt of lanthanum, of tungsten, of molybdenum, of titanium or of zirconium, or a solution comprising copper salts, aluminum salts and at least one of the salts of lanthanum, of tungsten, of molybdenum, of titanium or of zirconium, are precipitated in parallel or successively with a soda solution. The precipitated material is subsequently dried and optionally calcined.
B) Precipitation of a copper salt solution and of a solution of at least one salt of lanthanum, of tungsten, of molybdenum, of titanium or of zirconium, or of a solution comprising copper salt and at least one salt of lanthanum, of tungsten, of molybdenum, of titanium or of zirconium, onto a prefabricated aluminum oxide support. In a particularly preferred embodiment, this is present in the form of powder in an aqueous suspension. However, the support material may also be present in the form of spheres, extrudates, spall or tablets.

B1) In one embodiment (I), a copper salt solution and a solution of at least one salt of lanthanum, of tungsten, of molybdenum, of titanium or of zirconium, or a solution comprising copper salt and at least one salt of lanthanum, of tungsten, of molybdenum, of titanium or of zirconium, are precipitated, preferably with soda solution. The initial charge used is an aqueous suspension of the aluminum oxide support material.

Precipitated solids which result from A) or B) are filtered in a customary manner and preferably washed to free them of alkali, as described, for example, in DE 198 09 418.3.

Both the end products from A) and those from B) are dried at temperatures of 50 to 150° C., preferably at 120° C., and then optionally calcined, preferably at generally 200 to 600° C., especially at 300 to 500° C., for 2 hours.

The starting substances used for A) and/or B) may in principle be all Cu(I) and/or Cu(II) salts which are soluble in the solvents used in the application, for example nitrates, carbonates, acetates, oxalates or ammonium complexes, analogous aluminum salts and salts of lanthanum, of tungsten, of molybdenum, of titanium or of zirconium. Particular preference is given to using copper nitrate for processes according to A) and B).

In the process according to the invention, the above-described dried and optionally calcined powder is preferably processed to tablets, rings, ring tablets, extrudates, honeycombs or similar shaped bodies. For this purpose, all suitable prior art processes are conceivable.

The composition of the oxidic material is generally such that the proportion of copper oxide is in the range from 40 to 90% by weight, the proportion of oxides of lanthanum, of tungsten, of molybdenum, of titanium or of zirconium in the range from 0 to 50% by weight, and the proportion of aluminum oxide in the range up to 50% by weight, based in each case on the total weight of the sum of the abovementioned oxidic constituents, these three oxides together constituting at least 80% by weight of the oxidic material after calcination, cement not being counted among the oxidic material in the above sense.

In a preferred embodiment, the present invention therefore relates to a process as described above, wherein the oxidic material comprises
(a) copper oxide with a proportion in the range of $50 \leq x \leq 80$ and preferably $55 \leq x \leq 75\%$ by weight,
(b) aluminum oxide with a proportion in the range of $15 \leq y \leq 35$ and preferably $20 \leq y \leq 30\%$ by weight and
(c) at least one of the oxides of lanthanum, of tungsten, of molybdenum, of titanium or of zirconium with a proportion in the range of $2 \leq z \leq 20$ and preferably $3 \leq z \leq 15\%$ by weight,
based in each case on the total weight of the oxidic material after calcination, where: $80 \leq x+y+z \leq 100$, especially $95 \leq x+y+z \leq 100$.

The process according to the invention and the catalysts used for the hydrogenation are notable in that the addition of lanthanum, of tungsten, of molybdenum, of titanium or of zirconium in the course of precipitation leads to a high stability of the shaped body used as a catalyst.

In general, pulverulent copper, copper flakes or pulverulent cement or graphite or a mixture thereof is added to the oxidic material in the range from 1 to 40% by weight, preferably in the range from 2 to 20% by weight and more preferably in the range from 3 to 10% by weight, based in each case on the total weight of the oxidic material.

The cement used is preferably an alumina cement. The alumina cement more preferably consists essentially of aluminum oxide and calcium oxide, and it more preferably consists of about 75 to 85% by weight of aluminum oxide and about 15 to 25% by weight of calcium oxide. In addition, a cement based on magnesium oxide/aluminum oxide, calcium oxide/silicon oxide and calcium oxide/aluminum oxide/iron oxide can be used.

More particularly, the oxidic material may have, in a proportion of at most 10% by weight, preferably at most 5% by weight, based on the total weight of the oxidic material, at least one further component selected from the group consisting of the elements Re, Fe, Ru, Co, Rh, Ir, Ni, Pd and Pt.

In a further preferred embodiment of the process according to the invention, graphite is added to the oxidic material before the shaping to the shaped body in addition to the copper powder, the copper flakes or the cement powder or the mixture thereof. Preference is given to adding a sufficient amount of graphite that the shaping to a shaped body can be performed better. In a preferred embodiment, 0.5 to 5% by weight of graphite, based on the total weight of the oxidic material, is added. It is immaterial whether graphite is added to the oxidic material before or after or simultaneously with the copper powder, the copper flakes or the cement powder, or the mixture thereof.

Accordingly, the present invention also relates to a process as described above, wherein graphite is added in a proportion in the range from 0.5 to 5% by weight, based on the total weight of the oxidic material, to the oxidic material or to the mixture resulting from (ii).

In a preferred embodiment, in the process according to the invention, the catalyst precursor used for the hydrogenation may also be a shaped body comprising
an oxidic material which comprises
(a) copper oxide with a proportion in the range of $50 \leq x \leq 80$ and preferably $55 \leq x \leq 75\%$ by weight,
(b) aluminum oxide with a proportion in the range of $15 \leq y \leq 35$ and preferably $20 \leq y \leq 30\%$ by weight and
(c) at least one of the oxides of lanthanum, of tungsten, of molybdenum, of titanium or of zirconium with a proportion in the range of $2 \leq z \leq 20$ and preferably $3 \leq z \leq 15\%$ by weight,
based in each case on the total weight of the oxidic material after calcination, where: $80 \leq x+y+z \leq 100$, especially $95 \leq x+y+z \leq 100$,
metallic copper powder, copper flakes or cement powder or a mixture thereof with a proportion in the range from 1 to 40% by weight, based on the total weight of the oxidic material, and
graphite with a proportion of 0.5 to 5% by weight, based on the total weight of the oxidic material,
where the sum of the proportions of oxidic material, metallic copper powder, copper flakes or cement powder or a mixture thereof and graphite adds up to at least 95% by weight of the shaped body.

After adding the copper powder, the copper flakes or the cement powder or the mixture thereof and optionally graphite to the oxidic material, the shaped body obtained after the shaping is optionally calcined at least once over a period of generally 0.5 to 10 h, preferably 0.5 to 2 hours. The temperature in this at least one calcination step is generally in the range from 200 to 600° C., preferably in the range from 250 to 500° C. and more preferably in the range from 270 to 400° C.

In the case of shaping with cement powder, it may be advantageous to moisten the shaped body obtained before the calcination with water and then to dry it.

In a further embodiment, the shaped body obtained may also be treated with boiling water and/or steam before it is used for the hydrogenation.

In the case of use as a catalyst in the oxidic form, the shaped body, before being contacted with the hydrogenation solution, is prereduced with reducing gases, for example hydrogen, preferably hydrogen-inert gas mixtures, especially hydrogen/nitrogen mixtures, at temperatures in the range from 100 to 500° C., preferably in the range from 150 to 350° C. and especially in the range from 180 to 200° C. Preference is given to using a mixture with a hydrogen content in the range from 1 to 100% by volume, more preferably in the range from 1 to 50% by volume.

In a preferred embodiment, the inventive shaped body, before being used as a catalyst, is activated in a manner known per se by treatment with reducing media. The activation is effected either beforehand in a reduction oven or after installation in the reactor. When the reactor has been activated beforehand in the reduction oven, it is installed into the reactor and contacted directly with the hydrogenation solution under hydrogen pressure.

The process further provides a process for preparing 1,6-hexanediol, comprising the following steps:

a) oxidizing cyclohexane with oxygen or oxygen-comprising gases to give mixtures of cyclohexanol, cyclohexanone and carboxylic acids having up to six carbon atoms, b) reacting the reaction mixture obtained in a) with water and removing the DCS from the liquid biphasic reaction mixture, c) esterifying the DCS obtained from b) with an alcohol, d) catalytically hydrogenating the ester mixture obtained from c) and e) distilling the hydrogenation output obtained from d) to give 1,6-hexanediol, which comprises performing the esterification in c) with at least one diol having two to twelve carbon atoms and hydrogenating the esterification mixture obtained in c) in the liquid phase in the presence of a shaped catalyst body according to step d) whose precursor is obtainable by (i) providing an oxidic material comprising copper oxide, aluminum oxide and at least one of the oxides of lanthanum, of tungsten, of molybdenum, of titanium, of zirconium or of iron, (ii) adding pulverulent metallic copper, copper flakes, pulverulent cement, graphite or a mixture thereof to the oxidic material from step i) and (iii) shaping the mixture resulting from (ii) to a shaped body.

This process according to the invention for preparing 1,6-hexanediol, and also the process according to the invention for hydrogenating oligo- and/or polyesters, uses, as the starting material, the aqueous solutions of carboxylic acids which are formed as by-products in the oxidation of cyclohexane to cyclohexanol and cyclohexanone (cf. Ullmann's Encyclopedia of Industrial Chemistry, 6th ed., vol. 10, p. 282, FIG. 2), referred to hereinafter as dicarboxylic acid solution (DCS). These dicarboxylic acid solutions comprise (calculated without water in % by weight) generally between 10 and 40% adipic acid, between 10 and 60% 6-hydroxycaproic acid, between 1 and 10% glutaric acid, between 1 and 10% 5-hydroxyvaleric acid, between 0.5 and 5% 5-formylvaleric acid, between 1 and 5% 1,2-cyclohexanediols, between 1 and 5% 1,4-cyclohexanediols, between 2 and 10% formic acid, and a multitude of further mono- and dicarboxylic acids, esters, oxo and oxa compounds, the individual contents of which generally do not exceed 5%. Examples include acetic acid, propionic acid, butyric acid, valeric acid, caproic acid, oxalic acid, malonic acid, dihydromuconic acid, succinic acid, 4-hydroxybutyric acid, gamma-butyrolactone and caprolactone as mono- and dicarboxylic acids, esters, oxo and oxa compounds.

A closer analysis of the DCS found, as further constituents, 1,4-cyclohexanedione and 4-hydroxycyclohexanone in amounts of 0.01 to 2% by weight.

The DCS is generally an aqueous solution with a water content of 20 to 80% by weight.

Of the constituents of the DCS, adipic acid, 5-formylvaleric acid, 6-hydroxycaproic acid, dihydromuconic acid and caprolactone can be converted to 1,6-hexanediol by hydrogenation. In order to obtain pure 1,6-hexanediol, all other components must be removed between process steps c) to e).

Aldehydes such as 5-formylvaleric acid and ketones such as 1,4-cyclohexanedione and 4-hydroxycyclohexanone can form acetals and ketals in the course of the later esterification with diols. As a result of this, 5-formylvaleric acid can be lost by further reactions of the acetals for the preparation of 1,6-hexanediol. As a result of the acetal or ketal formation, the alcohol bound in each case can be lost entirely or partly.

According to the composition of the DCS, it may therefore be advantageous to catalytically hydrogenate the aldehydes and ketones present to alcohols before the esterification step c).

When the cyclohexane oxidation has been performed in the absence of a deperoxidation catalyst, for example cobalt naphthenate, the DCS comprises 6-hydroperoxycaproic acid, as described in DE-A 1 951 250 and EP-A 847 979. When oxidation has been effected in the presence of a deperoxidation catalyst, 6-hydroperoxycaproic acid is present only in small amounts.

When the cyclohexane oxidation has been performed without catalyst, the 6-hydroperoxycaproic acid formed, just like 5-formylvaleric acid, must be hydrogenated to 6-hydroxycaproic acid. This hydrogenation takes place before step c) of the process according to the invention.

Since the hydrogenation, which optionally takes place before step c) of the process according to the invention, must hydrogenate a hydroperoxy group in one case and an aldehyde group in another, the optimal hydrogenation conditions for the two compounds differ.

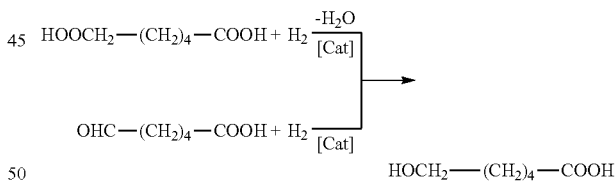

Since the hydroperoxycaproic acid can also be converted purely thermally to 6-hydroxycaproic acid, but less selectively than in the case of a hydrogenation, it is hydrogenated according to DE-A 1 951 250 in the presence of palladium, rhodium or platinum catalysts at 15 to 130° C., preferably 50 to 100° C., i.e. at moderate temperatures.

Keto and aldehyde groups are not hydrogenated under the conditions of the 6-hydroperoxycaproic acid hydrogenation in DE-A 1 951 250. For this purpose, higher temperatures and pressures are needed.

The hydrogenation of the DCS which is optionally performed before step c) of the process according to the invention can be performed in one reactor or in two reactors connected in series. When two reactors are used, the two reactors may comprise the same catalyst or two different catalysts. At the same time, the two reactors may differ in hydrogenation temperature and partial hydrogen pressure.

It is additionally possible to perform the hydrogenation which is optionally performed before step c) of the process according to the invention in a reactor filled only with a catalyst, in such a way that the hydrogenation temperature in the reactor rises within a desired temperature range.

The hydrogenation which is optionally performed before step c) of the process according to the invention is effected at 10 to 200° C., preferably 30 to 180° C., more preferably 50 to 170° C. The partial hydrogen pressure is 1 to 100 bar, preferably 10 to 80 bar, more preferably 30 to 60 bar.

For the catalytic hydrogenation which is optionally performed before step c) of the process according to the invention, the catalysts used comprise at least one metal of groups 7 to 12 of the periodic table, for example ruthenium, palladium, rhodium, nickel, cobalt, iron, rhenium, platinum, iridium, copper, osmium and zinc.

Additionally very suitable are what are known as unsupported catalysts, which do not comprise a support and consist of metals, metal oxides or mixtures thereof. Preference is given to unsupported iron and especially cobalt catalysts.

Preference is given in this case to the metals palladium, ruthenium, nickel, cobalt, rhenium and copper. These metals can be used either in the form of the metals or compounds thereof, for example oxides and sulfides.

The metals or metal compounds can be used without supports. However, they are preferably applied to supports, for example $TiO_2$, $Al_2O_3$, $ZrO_2$, $SiO_2$, $HfO_2$, carbon, zeolites or mixtures thereof. These supported catalysts can be used in a wide variety of finished forms, for example extrudates, tablets or rings.

Copper, nickel and cobalt can preferably be used in the form of Raney nickel, Raney copper or Raney cobalt. The Raney catalysts can also be used in all known finished forms, for example as tablets, extrudates or granules. Suitable Raney copper catalysts are, for example, Raney copper nuggets which are described in WO 99/03801.

Additionally particularly suitable for the hydrogenation which is optionally performed before step c) of the process according to the invention is a catalyst comprising ruthenium supported on shaped titanium dioxide bodies, said shaped titanium dioxide bodies being obtained by treating commercial titanium dioxide before or after shaping with 0.1 to 30% by weight of an acid in which titanium dioxide is sparingly soluble, which is used in the process according to the invention. Ruthenium can be used either in the form of the pure metal or of a compound thereof, for example oxide or sulfide.

The catalytically active ruthenium is applied by processes known per se, preferably to prefabricated $TiO_2$ as the support material.

A titanium dioxide support suitable with preference for use in the ruthenium-comprising catalyst can be obtained according to DE 197 38 464 by treating commercial titanium dioxide before or after shaping with 0.1 to 30% by weight of an acid, based on titanium dioxide, in which titanium dioxide is sparingly soluble. Preference is given to using titanium dioxide in the anatase polymorph. Suitable acids of this kind are, for example, formic acid, phosphoric acid, nitric acid, acetic acid or stearic acid.

The active ruthenium component can be applied in the form of a ruthenium salt solution to the titanium dioxide support thus obtained in one or more impregnation stages. Subsequently, the impregnated support is dried and optionally calcined. It is, however, also possible to precipitate ruthenium out of a ruthenium salt solution, preferably with sodium carbonate, onto a titanium dioxide present as a powder in aqueous suspension. The precipitated solids are washed, dried, optionally calcined and shaped. In addition, it is possible to convert volatile ruthenium compounds, for example ruthenium acetylacetonate or ruthenium carbonyl, to the gas phase and apply them to the support in a manner known per se (chemical vapor deposition).

The supported catalysts thus obtained may be present in all known finished forms. Examples are extrudates, tablets or granules. Before they are used, the ruthenium catalyst precursors are reduced by treatment with hydrogenous gas, preferably at temperatures greater than 100° C. Before they are used in the process according to the invention, the catalysts are preferably passivated at temperatures of 0 to 50° C., preferably at room temperature, with oxygenous gas mixtures, preferably with air-nitrogen mixtures. It is also possible to install the catalyst into the hydrogenation reactor in oxidic form and to reduce it under reaction conditions.

The catalyst particularly preferred in accordance with the invention has a ruthenium content of 0.1 to 10% by weight, preferably of 2 to 6% by weight, based on the total weight of the catalyst composed of catalytically active metal and support. The inventive catalyst may have a sulfur content of 0.01 to 1% by weight, based on the total weight of the catalyst (sulfur determination: coulometric).

The ruthenium surface area is from 1 to 20 $m^2/g$, preferably from 5 to 15 $m^2/g$, and the BET surface area (determined to DIN 66 131) from 5 to 500 $m^2/g$, preferably from 50 to 200 $m^2/g$.

The catalysts optionally used in the hydrogenation before step c) of the process according to the invention have a pore volume of 0.1 to 1 ml/g. In addition, the catalysts are notable for a cutting hardness of 1 to 100 N.

The hydrogenation catalysts which are optionally used before step c) of the process according to the invention may be suspended in the reaction mixture. It is preferred to arrange them in fixed bed form in the hydrogenation reactor. The hydrogenation can be performed batchwise or preferably continuously. The reaction mixture can be passed over the catalyst in liquid phase mode or trickle mode.

For the esterification in step c) of the process according to the invention of the carboxylic acids present in the DCS, polyols, diols, but particularly alpha,omega-diols with two to twelve carbon atoms, or mixtures of these diols, are suitable. Examples of such polyhydric alcohols are glycerol, trimethylolpropane, propylene glycol, ethylene glycol, 1,3-propanediol, 1,4-butanediol, 1,5-pentanediol, 1,6-hexanediol, 1,2-cyclohexanediol, 1,4-cyclohexanediol, 1,8-octanediol, 1,10-decanediol, 1,12-dodecanediol or mixtures of these diols. Preference is given to 1,4-butanediol, 1,5-pentanediol, 1,6-hexanediol, 1,2-cyclohexanediol, 1,4-cyclohexanediol or mixtures of these diols. Particular preference is given to 1,6-hexanediol since this esterification alcohol corresponds to the target product of the hydrogenation.

It is additionally preferred, instead of pure 1,6-hexanediol, to use a portion of the hydrogenation output for the esterification of the DCS in step c) of the process according to the invention, and the majority for the distillative workup to give 1,6-hexanediol. The weight ratio of hydrogenation output for the esterification to hydrogenation output for obtaining 1,6-hexanediol is from 2.5:1 to 0.8:1, preferably from 1.5:1 to 0.9:1. The hydrogenation output comprises generally 60 to 90% by weight of 1,6-hexanediol, 2 to 10% by weight of 1,5-pentanediol, 1,4-butanediol, 1,2-cyclohexanediol and 1,4-cyclohexanediol (in each case less than 5% by weight), and additionally up to 5% by weight of monoalcohols, for example n-butanol, n-pentanol and n-hexanol, and 1 to 10% by weight of oligomeric or polymeric high boilers with respect to 1,6-hexanediol.

It is particularly preferred to use a portion of the hydrogenation output, after distillative removal of low boilers and high boilers, for the esterification of the DCS in step c) of the process according to the invention. Low and high boilers are understood to mean compounds which have lower and higher boiling points than the diols present in the hydrogenation output.

A diol, especially an alpha,omega-diol such as 1,6-hexanediol or a mixture of diols, is added to the DCS for the esterification in step c) of the process according to the invention. The diol mixture used may be a portion of the hydrogenation output or a portion of the hydrogenation output after removal of high and low boilers. The mass ratio of DCS to diols is 1:0.2 to 1:0.8, preferably 1:0.3 to 1:0.7, more preferably 1:0.4 to 1:0.6.

Water removal in step b) and esterification in step c) of the process according to the invention are preferably performed in one process step. For this purpose, it is possible to use stirred reactors, flow tubes and/or columns. Preference is given to removing water and esterifying in at least one reactor with an attached distillation column. In order to achieve complete conversion in the esterification of the carboxylic acids and complete water removal, 2 to 6 and preferably 3 to 5 series-connected reactors with attached columns are employed.

The esterification reaction to give oligo- and/or polyesters of the DCS, and in step c) of the process according to the invention, can proceed without addition of a catalyst. However, it is also possible to increase the reaction rate by adding a catalyst for the esterification. This may be a homogeneous, dissolved or heterogeneous catalyst.

Examples of homogeneous catalysts for the esterification include sulfuric acid, phosphoric acid, hydrochloric acid, sulfonic acids such as p-toluenesulfonic acid, heteropolyacids such as tungstophosphoric acid, or Lewis acids, for example aluminum, vanadium, titanium or boron compounds, Preference is given to mineral acids, especially sulfuric acid. The weight ratio of homogeneous catalyst to carboxylic acid is generally 0.0001 to 0.5, preferably 0.001 to 0.3.

Suitable heterogeneous catalysts are acidic or superacidic materials, for example acidic and superacidic metal oxides such as $SiO_2$, $Al_2O_3$, $SnO_2$, $ZrO_2$, sheet silicates or zeolites, all of which may be doped with mineral acid residues such as sulfate or phosphate for acid strengthening, or organic ion exchangers with sulfonic acid or carboxylic acid groups. The solid catalysts may be arranged in fixed bed form or be used as a suspension.

Preference is given to esterifying without catalyst.

The bottom temperature in the reactors with attached column is 200 to 250° C. The esterification and water removal can be performed at pressures of 0.1 to 5 bar, preferably 0.5 to 3 bar, more preferably at 1 bar. The residence time calculated over all stirred tanks is 0.5 to 12 hours, preferably 1 to 11 hours, more preferably 2 to 10 hours.

The top product obtained in the attached columns is the water present in the DCS and that formed in the esterification. The top product may further comprise organic by-products, for example lower monocarboxylic acids, e.g. formic acid.

The bottom product obtained from the last reactor is a mixture of oligo- and polyesters, which formed from the carboxylic acids present in the DCS, the cyclodiols and the added diols. The bottom product also comprises unconverted diols. This mixture is used for the subsequent catalytic hydrogenation in step d) of the process according to the invention.

The completeness of the conversion of the free carboxyl groups present in the carboxylic acid mixture is determined with the acid number (mg KOH/g) measured after the esterification. Minus any acid added as a catalyst, it is 1 to 20, preferably 2 to 15 and more preferably 5 to 10 mg KOH/g.

When a dissolved acid has been used as a catalyst for esterification, the ester mixture is appropriately neutralized with a base, 1 to 1.5 base equivalents being added per acid equivalent of the catalyst. The bases used are generally alkali metal or alkaline earth metal oxides, carbonates, hydroxides or alkoxides, or amines in substance or dissolved in the esterification alcohol.

The hydrogenation of the oligo- and/or polyester mixture and the hydrogenation in step d) of the process according to the invention are effected catalytically in the liquid phase in the presence of fixed bed or suspended, preferably fixed bed, catalysts. The temperatures employed are between 100 and 350° C., preferably 120 and 300° C., more preferably 140° C. and 280° C., and the pressures from 30 to 350 bar, preferably 40 to 320 bar, more preferably 50 to 300 bar. The catalyst hourly space velocity is 0.2 to 1.5 kg of oligoester/kg of catalyst×h.

The hydrogenation of the oligo- and/or polyester mixture and the hydrogenation in step d) of the process according to the invention can in principle be performed in only one reactor. However, this method has disadvantages: ester hydrogenations are strongly exothermic and additionally have to be performed at high temperatures. For instance, the hydrogenation temperature according to U.S. Pat. No. 3,524,892, where the hydrogenation of oligoesters prepared from DCS was effected in the presence of barium oxide-doped copper chromite, is 260 to 270° C. For safe removal of heat from the reactor, a high level of complexity has to be employed.

Therefore, the hydrogenation of the oligo- and/or polyester mixture and the hydrogenation in step d) of the process according to the invention is preferably performed in at least two reactors connected in series. When fixed bed catalysts are employed, the hydrogenation feed can be passed over the catalyst in liquid phase mode or trickle mode. When working in liquid phase mode, hydrogen gas is introduced into the reactor flooded with the liquid reaction mixture, and the hydrogen passes through the catalyst bed in ascending gas bubbles. When working in trickle mode, the liquid ester mixture, in the reactor under hydrogen pressure, is allowed to trickle over the catalyst bed arranged therein, which forms a thin liquid film on the catalyst.

In a particularly preferred embodiment, a plurality of reactors are used, in which case the predominant portion of the esters is hydrogenated in the first reactor, up to a conversion of 80 to 98%, preferably of 90 to 95%. The first reactor is preferably operated with liquid circulation for heat removal by means of heat exchangers, and the downstream reactor(s) preferably in straight pass, without circulation to complete the conversion. This method is referred to as the circulation method.

The hydrogenation of the oligo- and/or polyester mixture and the hydrogenation in step d) of the process according to the invention can be effected batchwise, preferably continuously.

The hydrogenation of the oligo- and/or polyester mixture and the hydrogenation in step d) of the process according to the invention is generally performed with the ester mixture which is obtained in the esterification and comprises excess diols, without additional solvent. However, it may also be advantageous to work in the presence of a solvent which is inert under the reaction conditions. Useful solvents include, for example, all diols used for the esterification, and also tetrahydrofuran, dioxane and monoalcohols having 1 to 6 carbon atoms, for example methanol, ethanol, propanols, n-butanol, n-hexanol or mixtures of the compounds mentioned. The amount of solvent is 5 to 50% by weight, preferably 10 to 30% by weight, based on the ester mixture.

Preference is given to performing the hydrogenation of the oligo- and/or polyester mixture and the hydrogenation in step d) of the process according to the invention without solvent.

It may also be advantageous to meter a base into the ester mixture obtained in the esterification. Preference is given to using lithium alkoxides, sodium alkoxides and potassium alkoxides, particular preference to using sodium methoxide. The amount of base is 20 to 180 ppm, preferably 30 to 90 ppm, based on the ester mixture. In the case of an ester mixture with a residual acid number of >1 mg KOH/g, the residual acids are neutralized only in insignificant amounts. The base added serves to suppress the formation of by-products which might otherwise form in the hydrogenation, for example hexanol or ether compounds.

The hydrogenation of the oligo- and/or polyester mixture and the hydrogenation in step d) of the process according to the invention is effected in the presence of the shaped catalyst precursor body which, in addition to copper oxide, aluminum oxide and at least one of the oxides of lanthanum, of tungsten, of molybdenum, of titanium, of zirconium or of iron, also comprises metallic copper, copper flakes, pulverulent cement, graphite or a mixture, as already described in the process for hydrogenating the oligo- and polyesters of DCS comprising diols. The catalyst and preparation thereof are described in WO 2004/085356, WO 2006/005505 and WO 2007/006719.

Before being used as a catalyst, the shaped bodies are activated in a manner known per se by treatment with reducing media. The activation is effected either beforehand in a reduction oven or after installation in the reactor. When the catalyst precursor has been activated beforehand in the reduction oven, it is installed into the reactor and contacted directly with the hydrogenation solution under hydrogen pressure.

The hydrogenation of the oligo- and/or polyester mixture and the hydrogenation in step d) of the process according to the invention achieve a high oligo- and polyester conversion. The conversion in the presence of the inventive catalysts is more than 90%, preferably more than 95%, more preferably more than 99%. Unconverted oligo- and polyesters are high boilers with respect to 1,6-hexanediol, and are obtained as bottom products in the course of distillation.

Preference is given to using a portion of the hydrogenation output in step e) of the process according to the invention, which is a mixture of diols, instead of pure 1,6-hexanediol for the esterification of the DCS. The advantage of this process is that other diols such as 1,5-pentanediol, 1,4-butanediol, 1,4-cyclohexanediol, 1,2-cyclohexanediol, some of which constitute by-products, replace the 1,6-hexanediol. This significantly reduces losses of 1,6-hexanediol which enters into side reactions.

In a first column, the hydrogenation output is freed of high and low boilers with respect to the diols 1,6-hexanediol, 1,5-pentanediol, 1,4-butanediol, 1,4-cyclohexanediol, 1,2-cyclohexanediol. The column has 1 to 30 theoretical plates. The bottom temperatures employed are 120 to 250° C., and the pressures 5 to 500 mbar.

The top product comprises 75 to 95% by weight of 1,6-hexanediol, 3 to 10% by weight of 1,5-pentanediol, 1,4-butanediol, 1,2-cyclohexanediol and 1,4-cyclohexanediol (less than 5% by weight of each), and also up to 5% by weight of monoalcohols, for example n-butanol, n-pentanol and n-hexanol, and less than 5% by weight of higher-boiling components with respect to 1,6-HDO.

The bottom product comprises unconverted oligo- and polyesters. Since the oligo- and polyester conversion is up to ≥97%, the bottom product comprises ≤3% of products hydrogenatable to 1,6-hexanediol. It can therefore be discarded.

The distillate obtained is passed into a second column, in which the fine purification of the 1,6-hexanediol is effected. This achieves 1,6-hexanediol purities of >97%.

In a particularly preferred embodiment of the esterification in step c) of the process according to the invention, a portion of the hydrogenation output which has been freed of high and low boilers is recycled into the esterification in step c). This variant has the additional advantage that the product streams in the process are reduced in size.

The process according to the invention thus allows, in an economically viable manner, pure 1,6-hexanediol to be obtained from a waste product.

It was not foreseeable that the inventive catalyst, in the case of use of oligoesters as the feed and residual acid numbers of 1 to 20, would retain a high activity over long reaction times (example: 900 hours), coupled with high side crushing strength and hence high mechanical strength.

An additional factor is that, in accordance with the invention, at ≥95%, significantly higher 1,6-hexanediol yields are achieved than according to the prior art.

WORKING EXAMPLE

Preparation of 1,6-hexanediol (1,6-HDO) from a Dicarboxylic Acid Solution (DCS) by Esterification with a Diol Mixture, Subsequent Hydrogenation and Workup 1. Blending of a Dicarboxylic Acid-Crude Hexanediol Mixture The dicarboxylic acid solution used was obtained by water extraction of a reaction output which originated from the oxidation of cyclohexane with air.

The crude 1,6-hexanediol mixture was prepared from the hydrogenation output of the oligo- and polyester hydrogenation (see 4a/b) by distillative removal of high and low boilers (with respect to the diols).

337 kg of a crude 1,6-hexanediol mixture were added to 750 kg of a DCS (acid number: 267 mg KOH/g) comprising, inter alia, adipic acid (ADA, 21% by weight), 6-hydroxycaproic acid (HCA, 18% by weight) and water (45% by weight), partly in the form of oligomers. The crude 1,6-HDO charge comprises, inter alia, 1,6-hexanediol (approx. 80% by weight), 1,5-pentanediol, 1,4-butanediol, 1,4-cyclohexanediol and 1,2-cyclohexanediol. The aqueous solution formed (DCS-HDO mixture) comprised 1,6-HDO (23% by weight), ADA (15% by weight) and HCA (12.0% by weight) as main components (partly in the form of oligomers).

2. Preparation of an Oligomeric Ester Mixture

The DCS-HDO mixture of stage 1 was metered continuously into an evaporator (dewatering stage, 150° C., ambient pressure) at a throughput of 260 g/h. This distilled off water and low-boiling components (98 g/h). The bottoms discharge was subsequently transferred into a 5-stage stirred tank cascade (174 g/h, 220° C., 1-1.4 bar abs.), in which the esterification was brought to almost complete conversion (AN<10 mg KOH/g, 98% conversion). In the ester cascade, low-boiling components were likewise distilled off (12 g/h) and were recycled into the dewatering stage. The bottoms discharge obtained was an oligomeric mixture comprising principally esters formed from the carboxylic acid derivatives and diols originally supplied (162 g/h, 62% yield by weight, based on the overall feed).

3. Hydrogenation of the Oligomeric Ester Mixture

The oligomeric esters of stage 2 were admixed with 60 ppm of sodium methoxide and then hydrogenated continuously over a copper catalyst. The catalyst was prepared and activated according to WO 2007/6719 example 3.

The reactor system consisted of a main reactor (tubular reactor, 400 ml, 600 g of catalyst) and a postreactor (tubular reactor, 100 ml, 150 g of catalyst). The hydrogenation feed was passed over the fixed bed catalyst in trickle mode. In order to remove the heat which evolves in the course of hydrogenation, the main reactor was operated with liquid circulation, and the postreactor in straight pass. The hydrogenation reactor was operated at 240° C./255 bar of $H_2$ for 900 h. At a feed rate of 240 g/h (catalyst hourly space velocity=0.60 $kgl^{-1}h^{-1}$, main reactor), a conversion of 98% was achieved. The hydrogenation output was subsequently decompressed to ambient pressure and cooled to ambient temperature in a vessel. This afforded outputs whose 1,6-hexanediol content was 72% by weight. The hydrogenation proceeded with >95% yield to 1,6-HDO (the yield is based on the C6 components which are present in the DCS and can lead to 1,6-HDO by hydrogenation: 6-hydroxycaproic acid, 6-oxocaproic acid (5-formylvaleric acid), adipic acid and dihydromuconic acid). The catalyst was deinstalled and then analyzed. The deinstalled catalyst had a side crushing strength of 31 N (original catalyst: 48 N).

The 1,6-hexanediol content was determined by GC: DB-5 (Agilent J&W), 30 m×0.2 mm×1 µm; temperature profile: 60° C. (5 min)→220° C. (16° C./min, 10 min)→260° C. (20° C./min, 21 min)→290° C. (20° C./min, 10 min). Diethylene glycol dimethyl ether (DEGDME) was used as an internal standard, $t_R$(DEGDME)=8.8 min, $t_R$(1.6–HDO)=11.8 min.

4 a Removal of High and Low Boilers from the Hydrogenation Output

In a distillation still with an attached column (DN50, 1 m internals, 750 $m^2/m^3$ fabric packing), hydrogenation outputs (917 g) from stage 3 were separated by distillation. At 1 bar and bottom temperature 150° C., low boilers (25 g) were removed. Subsequently, the pressure was reduced to 150 mbar and the bottom temperature increased up to 225° C. 30% of the distillate obtained was recycled to the column at the top; the predominant portion was collected. 840 g of distillate were obtained (comprised, inter alia, 79% by weight of 1,6-HDO, 9% by weight of 1,5-PDO). The high boilers accumulated in the bottoms (41 g, 4.5% by weight). A portion of the distillates collected is blended with the DCS as the crude 1,6-HDO charge (see stage 1), while the other portion is transferred into the purifying distillation.

4 b Purifying Distillation

A crude 1,6-HDO charge from the high boiler removal was fractionally distilled at 50 mbar (return ratio of 10:1, top draw of approx. 50 g/h). After removal of other low-boiling diols (including 1,5-pentanediol), 1,6-HDO was obtained with a purity of >97%.

The invention claimed is:

1. A process for hydrogenating at least one oligo- or polyester comprising:
hydrogenating the at least one oligo- or polyester in the presence of a shaped catalyst body whose precursor is obtained by a process comprising:
(i) combining
an oxidic material comprising copper oxide, aluminum oxide and at least one additional metal oxide of a metal selected from the group consisting of lanthanum, tungsten, molybdenum, titanium, zirconium, and iron, and at least one second material selected from the group consisting of pulverulent metallic copper, copper flakes, pulverulent cement, graphite, and a mixture thereof with the oxidic material to obtain a catalyst precursor mixture,
(ii) shaping the catalyst precursor mixture to obtain the shaped catalyst body, and
(iii) calcining the shaped catalyst body
wherein the oxidic material is obtained by simultaneous or successive precipitation of an active copper component, an aluminum component, and a component of at least one of oxide of a metal selected from the group consisting of lanthanum, tungsten, molybdenum, titanium, and zirconium, subsequent drying and a first calcination
and wherein the at least one oligo- or polyester is obtained by esterifying a dicarboxylic acid solution with a diol or diol mixture, then adding a base selected from the group consisting of lithium alkoxide, potassium alkoxide, and sodium alkoxide, wherein the dicarboxylic acid solution comprises dicarboxylic acids obtained as a waste product in the oxidation of cyclohexane with air to give cyclohexanone and cyclohexanol, by extraction of the oxidized mixture with water.

2. The process according to claim 1, wherein the oxidic material comprises
(a) copper oxide with a proportion, x, in a range of 50 to 80% by weight,
(b) aluminum oxide with a proportion, y, in a range of 15 to 35% by weight, and
(c) at least one of the oxides of lanthanum, of tungsten, of molybdenum, of titanium or of zirconium with a proportion, z, in a range of 2 to 20% by weight,
based in each case on total weight of the oxidic material excluding cement after calcination, where $80 \leq x+y+z \leq 100$.

3. The process of claim 1, wherein a content of the at least one second material is from 0.5 to 40% by weight, based on the total weight of the oxidic material, after the first calcination.

4. The process of claim 1, wherein the diol or diol mixture comprises at least one alpha,omega-diol having two to twelve carbon atoms or mixtures thereof.

5. The process of claim 1, wherein the shaped catalyst body is further treated with at least one treating material selected from the group consisting of boiling water and steam.

6. A process for preparing 1,6 hexanediol, comprising:
a) oxidizing cyclohexane, in a cyclohexane oxidation, with at least one oxygen-comprising gas to obtain a cyclohexane oxidation mixture comprising cyclohexanol, cyclohexanone, and at least one carboxylic acid having up to six carbon atoms,
b) reacting the cyclohexane oxidation mixture obtained in a) with water to obtain a liquid biphasic reaction mixture and removing a dicarboxylic acid solution from the liquid biphasic reaction mixture,
c) esterifying, in an esterification, the dicarboxylic acid solution obtained from b) with an alcohol, then adding a base selected from the group consisting of lithium alkoxide, potassium alkoxide and sodium alkoxide to obtain an ester mixture,
d) catalytically hydrogenating, in a hydrogenation, the ester mixture obtained from c) to obtain a hydrogenation output, and
e) distilling, in a distillation, the hydrogenation output obtained from d) to obtain a distilled hydrogenation output, wherein a substance selected from the group consisting of at least one diol having two to twelve carbon atoms and a portion of the hydrogenation output obtained in e) is present during the esterification, and wherein hydrogenation is in the liquid phase in the presence of a shaped catalyst body whose precursor can be prepared by a process comprising:

(i) combining
- an oxidic material after a first calcination comprising copper oxide, aluminum oxide and at least one additional metal oxide of a metal selected from the group consisting of lanthanum, tungsten, molybdenum, titanium, zirconium, and iron, and
- at least one second material selected from the group consisting of pulverulent metallic copper, copper flakes, pulverulent cement, graphite and a mixture thereof with the oxidic material to obtain a catalyst precursor mixture, (ii) shaping the catalyst precursor mixture to a shaped body and (iii) calcining, in a second calcination, the shaped body.

7. The process according to claim 6, wherein the cyclohexane oxidation is conducted in the presence of a catalyst.

8. The process of claim 6, wherein an aqueous phase of the liquid biphasic reaction mixture obtained in b) is catalytically hydrogenated at a temperature in the range from 10 to 200° C. and a pressure of 1 to 100 bar.

9. The process of claim 6, wherein 1,6-hexanediol is present during the esterification in c).

10. The process of claim 6, further comprising:
removing high and low boilers from the distilled hydrogenation output obtained in e) to obtain a portion of the distilled hydrogenation output, and
esterifying, in the esterification in c), in the presence of the portion of the distilled hydrogenation output.

11. The process of claim 6, wherein an acid number of the ester mixture is 1 to 20 mg KOH/g.

12. The process of claim 6, wherein the hydrogenation in d) is performed in the liquid phase in at least two reactors, the first reactor for removal of heat with liquid recycling, the second reactor for completion of the conversion in straight pass without liquid recycling.

13. The process according to claim 2, wherein the oxidic material comprises copper oxide with a proportion, x, in a range of 55 to 75% by weight.

14. The process according to claim 2, wherein the oxidic material comprises aluminum oxide with a proportion, y, in a range of 20 to 30% by weight.

15. The process according to claim 2, wherein the oxidic material comprises at least one of the oxides of lanthanum, of tungsten, of molybdenum, of titanium or of zirconium with a proportion, z, in a range of 3 to 15% by weight.

16. The process according to claim 2, wherein a sum x+y+z is in a range of 95 to 100%.

\* \* \* \* \*